(12) United States Patent
Mokelke et al.

(10) Patent No.: US 9,839,785 B2
(45) Date of Patent: Dec. 12, 2017

(54) SURGICAL INSTRUMENT FOR IMPLANTING LEADS FOR BARORECEPTOR STIMULATION THERAPY

(71) Applicant: Cardiac Pacemakers, Inc., St. Paul, MN (US)

(72) Inventors: Eric A. Mokelke, Flagstaff, AZ (US); Eric F Hammill, Ham Lake, MN (US); Brian Soltis, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 489 days.

(21) Appl. No.: 14/569,455

(22) Filed: Dec. 12, 2014

(65) Prior Publication Data

US 2015/0165215 A1    Jun. 18, 2015

Related U.S. Application Data

(60) Provisional application No. 61/915,538, filed on Dec. 13, 2013.

(51) Int. Cl.
| | | |
|---|---|---|
| *A61B 5/04* | (2006.01) |
| *A61N 1/372* | (2006.01) |
| *A61B 17/02* | (2006.01) |
| *A61N 1/05* | (2006.01) |
| *A61N 1/36* | (2006.01) |

(52) U.S. Cl.
CPC .......... *A61N 1/372* (2013.01); *A61B 17/0206* (2013.01); *A61N 1/0526* (2013.01); *A61N 1/36117* (2013.01)

(58) Field of Classification Search
CPC .............. A61B 17/0206; A61N 1/0526; A61N 1/36117; A61N 1/372
See application file for complete search history.

(56) References Cited

U.S. PATENT DOCUMENTS

| | | |
|---|---|---|
| 5,476,493 A | 12/1995 | Muff |
| 5,674,272 A | 10/1997 | Bush et al. |
| (Continued) | | |

FOREIGN PATENT DOCUMENTS

| | | |
|---|---|---|
| CN | 101244315 A | 8/2008 |
| CN | 102438696 A | 5/2012 |
| (Continued) | | |

OTHER PUBLICATIONS

International Search Report arid Written Opinion issued in PCT/US2015/036526, dated Oct. 26, 2015, 12 pages.

(Continued)

*Primary Examiner* — George Manuel
(74) *Attorney, Agent, or Firm* — Faegre Baker Daniels LLP

(57) ABSTRACT

The present disclosure presents methods and apparatuses for mapping a target physiological region, for example, during baroreceptor stimulation therapy. In an aspect, such an example apparatus of the present disclosure may include a surgical instrument configured to be securely coupled to a patient and to allow access to a target physiological region. Furthermore, the example apparatus may include an attachment element coupled to the surgical instrument and configured to releasably engage a lead, stabilize the lead during mapping of the target physiological region, and allow the lead to be repositioned relative to the target physiological region.

17 Claims, 8 Drawing Sheets

(56) References Cited

U.S. PATENT DOCUMENTS

| | | |
|---|---|---|
| 6,564,079 B1 | 5/2003 | Cory et al. |
| 6,909,920 B2 | 6/2005 | Lokhoff et al. |
| 6,985,774 B2 | 1/2006 | Kieval et al. |
| 7,006,875 B1 | 2/2006 | Kuzma et al. |
| 7,015,061 B2 | 3/2006 | Lu et al. |
| 7,337,005 B2 | 2/2008 | Kim et al. |
| 7,445,953 B2 | 11/2008 | Lu et al. |
| 7,502,650 B2 | 3/2009 | Kieval |
| 7,616,997 B2 | 11/2009 | Kieval et al. |
| 7,813,812 B2 | 10/2010 | Kieval et al. |
| 8,126,560 B2 | 2/2012 | Scheiner et al. |
| 8,175,705 B2 | 5/2012 | Libbus |
| 8,571,664 B2 | 10/2013 | Anderson et al. |
| 8,774,941 B2 | 7/2014 | Pianca |
| 8,901,268 B2 | 12/2014 | Krishnamoorthy et al. |
| 8,948,872 B2 | 2/2015 | Shuros et al. |
| 9,345,877 B2 | 5/2016 | Pignato et al. |
| 2002/0095080 A1 | 7/2002 | Cory et al. |
| 2003/0187490 A1 | 10/2003 | Gliner |
| 2004/0176759 A1 | 9/2004 | Krishnamurthy et al. |
| 2005/0085884 A1 | 4/2005 | O'Brien et al. |
| 2005/0096710 A1 | 5/2005 | Kieval |
| 2005/0182456 A1 | 8/2005 | Ziobro et al. |
| 2006/0085049 A1 | 4/2006 | Cory et al. |
| 2006/0276704 A1 | 12/2006 | McGinnis et al. |
| 2007/0021792 A1 | 1/2007 | Kieval et al. |
| 2007/0027512 A1 | 2/2007 | Chan et al. |
| 2007/0208391 A1 | 9/2007 | Wahlstrand et al. |
| 2007/0213795 A1 | 9/2007 | Bradley et al. |
| 2008/0004673 A1 | 1/2008 | Rossing et al. |
| 2008/0046051 A1 | 2/2008 | Skubitz et al. |
| 2008/0046054 A1 | 2/2008 | Hjelle et al. |
| 2008/0147146 A1 | 6/2008 | Wahlgren et al. |
| 2009/0132002 A1 | 5/2009 | Kieval |
| 2009/0143837 A1 | 6/2009 | Rossing et al. |
| 2009/0234418 A1 | 9/2009 | Kieval et al. |
| 2010/0152826 A1 | 6/2010 | Tanabe et al. |
| 2010/0324641 A1 | 12/2010 | Skubitz et al. |
| 2011/0257716 A1 | 10/2011 | Tiedtke |
| 2012/0271389 A1* | 10/2012 | Cates ............... A61N 1/05 607/116 |
| 2013/0018247 A1 | 1/2013 | Glenn et al. |
| 2015/0018918 A1 | 1/2015 | Mokelke et al. |
| 2015/0165215 A1 | 6/2015 | Mokelke et al. |
| 2015/0231391 A1 | 8/2015 | Mokelke |
| 2015/0366465 A1 | 12/2015 | De Kock et al. |
| 2015/0366467 A1 | 12/2015 | De Kock et al. |
| 2016/0059005 A1 | 3/2016 | De Kock et al. |
| 2016/0074650 A1 | 3/2016 | De Kock et al. |

FOREIGN PATENT DOCUMENTS

| | | |
|---|---|---|
| EP | 1487535 B1 | 12/2004 |
| EP | 2108398 B1 | 10/2009 |
| EP | 1487535 B1 | 6/2012 |
| JP | 2004526471 A | 9/2004 |
| JP | 200951050 A | 5/2009 |
| JP | 2009532102 A2 | 9/2009 |
| JP | 2009532185 A | 9/2009 |
| JP | 2010505465 A | 2/2010 |
| JP | 2012130579 A | 7/2012 |
| JP | 2013541390 A | 11/2013 |
| KR | 20120053090 A | 5/2012 |
| WO | 2002026314 A1 | 4/2002 |
| WO | WO0226314 A1 | 4/2002 |
| WO | 2007118090 A2 | 10/2007 |
| WO | 2015195980 A1 | 12/2015 |
| WO | 2015195982 A2 | 12/2015 |

OTHER PUBLICATIONS

International Search Report and Written Opinion Issued in PCT/US2015/036528, dated Jan. 19, 2016, 15 pages.
Invitation to Pay Additional Fees and, Where Applicable, Protest Fee issued in PCT/US2015/036528, dated Oct. 28, 2015, 6 pages.
International Preliminary Report on Patentability issued in PCT/US2014/046008, dated Jan. 28, 2016, 8 pages.
International Preliminary Report on Patentability issued in PCT/US2015/036526 dated Dec. 20, 2016, 8 pages.
International Preliminary Report on Patentability issued in PCT/US2015/036528, dated Dec. 20, 2016, 9 pages.
International Search Report and Written Opinion] issued in PCT/US2014/046008, dated Oct. 1, 2014, 12 pages.
International Search Report and Written Opinion issued in PCT/US2015/050303, dated Jan. 14, 2016, 12 pages.
International Preliminary Report on Patentability issued in PCT/US2015050303, dated Mar. 30, 2017, 8 pages.

* cited by examiner

SURGICAL INSTRUMENT FOR IMPLANTING LEADS FOR BARORECEPTOR STIMULATION THERAPY

CROSS-REFERENCE TO RELATED APPLICATION

This application claims priority to Provisional Application No. 61/915,538, filed Dec. 13, 2013, which is herein incorporated by reference in its entirety.

TECHNICAL FIELD

The present invention relates to medical devices and methods for mapping a target physiological region of a patient. More specifically, the invention relates to devices and methods for mapping carotid sinus and vascular tissue easily and accurately.

BACKGROUND

Research suggests that electrical stimulation of baroreceptors on the carotid sinus can be used to treat hypertension. The baroreceptors on the carotid sinus can be electrically stimulated temporarily or permanently by placing electrodes on or near the carotid sinus, within which the baroreceptors are distributed. To locate optimal electrode placement positions for this stimulation, one way to identify the treatment location is to perform electrical mapping of the carotid sinus. Hence, there is a need to develop improved tools and techniques for facilitating the mapping of the baroreceptors located within the carotid sinus for delivery of chronic electrical therapy.

SUMMARY

In Example 1, a medical apparatus comprising a surgical instrument and an attachment element. The surgical instrument is configured to be securely coupled to a patient and to allow access to a target physiological region. The attachment element is coupled to the surgical instrument and is configured to releasably engage an implantable medical device lead. In some embodiments, the implantable medical device lead can be a chronically implanted lead. In some embodiments, the implantable medical device lead can be a temporary lead or an acute lead.

In Example 2, the medical apparatus of Example 1, wherein the implantable medical device lead comprises a lead body and an electrode portion, wherein the electrode portion comprises at least one electrode configured to apply at least one stimulation signal to the target physiological region, and wherein the surgical instrument is configured to urge the electrode portion into stable contact with the target physiological region when the surgical instrument is coupled to the patient.

In Example 3, the medical apparatus of either of Examples 1 or 2, further comprising a biasing element attached to at least one of the surgical instrument and the attachment element, wherein the biasing element is configured, in use, to urge the electrode portion of the implantable medical device lead toward the target physiological region and cause the electrode portion of the implantable medical device lead to apply pressure stably to the target physiological region when the implantable medical device lead is coupled to the attachment element and the surgical instrument is coupled to the patient.

In Example 4, the medical apparatus of Example 3, wherein the biasing element is composed at least in part of a pliant material and configured to urge the electrode portion of the implantable medical device lead toward the target physiological region upon an application of bending stress to the biasing element when the implantable medical device lead is coupled to the attachment element and the surgical instrument is coupled to the patient.

In Example 5, the medical apparatus of Example 3, wherein the biasing element comprises an axial adjustment element comprising an axial adjustment element support and an axial adjustment head, wherein a position of the axial adjustment head is selectively adjustable along an adjustment axis.

In Example 6, the medical apparatus of Example 5, wherein the axial adjustment head comprises an adjustment screw configured to cause the adjustment head to move along the adjustment axis upon rotation of the adjustment screw.

In Example 7, the medical apparatus of any of Examples 1-6, wherein the attachment element comprises a lead clip configured to receive and engage the lead body.

In Example 8, the medical apparatus of any of Examples 1-7, wherein the attachment element comprises a flexible arm configured to substantially enclose a portion of the lead body and release upon impetus from the user.

In Example 9, the medical apparatus of any of Examples 1-8, wherein the attachment element is releasably coupled to the surgical instrument.

In Example 10, the medical apparatus of any of Examples 1-9, wherein the surgical instrument is further configured to maintain visual access to the target physiological region when coupled to the patient.

In Example 11, the medical apparatus of any of Examples 1-10, wherein the surgical instrument includes first and second instrument portion each including a clamp portion and a handle portion opposite the clamp portion, wherein the first and second instrument portions are pivotally coupled to one another between the respective handle and clamp portions such that an application of an inward force urging the handle portions toward one another causes the clamp portions to separate from one another.

In Example 12, the medical apparatus of any of Examples 1-11, wherein the attachment element is coupled to one or both of the first and second instrument portions.

In Example 13, the medical apparatus of any of Examples 1-12, wherein the surgical instrument comprises a self-restraining retractor, such as a Weitlaner retractor, a Mayo-Adams retractor, a Rigby retractor, a Gelpi retractor, or another instrument fulfilling a similar function.

In Example 14, a medical kit comprising a surgical instrument, an attachment element and an implantable medical device lead. The surgical instrument is configured to be securely coupled to a patient and to allow access to a target physiological region. The attachment element is permanently or transiently coupled to the surgical instrument. The implantable medical device lead comprises a lead body and an electrode portion, wherein the electrode portion comprises at least one electrode configured to apply at least one stimulation signal to the target physiological region. The attachment element is configured to releasably engage the lead body and the surgical instrument is configured to urge the electrode portion into stable contact with the target physiological region when the lead body is engaged by the attachment element and the surgical instrument is coupled to the patient.

In Example 15, the medical kit of Example 14, wherein the lead body includes neck region proximal to the electrode portion, the neck region including a spring disposed within the lead body.

In Example 16, the medical kit of either of Examples 14 or 15, further comprising a biasing element attached to at least one of the surgical instrument and the attachment element, wherein the biasing element is configured, in use, to urge the electrode portion of the implantable medical device lead toward the target physiological region and cause the electrode portion of the implantable medical device lead to apply pressure to the target physiological region when the implantable medical device lead is coupled to the attachment element and the surgical instrument is coupled to the patient.

In Example 17, the medical apparatus of Example 16, wherein the biasing element is composed at least in part of a pliant material and configured to urge the electrode portion of the implantable medical device lead toward the target physiological region upon an application of bending stress to the biasing element when the implantable medical device lead is coupled to the attachment element and the surgical instrument is coupled to the patient.

In Example 18, the medical apparatus of Example 16, wherein the biasing element comprises an axial adjustment element comprising an axial adjustment element support and an axial adjustment head, wherein a position of the axial adjustment head is selectively adjustable along an adjustment axis.

In Example 19, a method of mapping a target physiological region of a patient. The method comprises coupling a surgical instrument to the patient to allow access to the target physiological region, and coupling a lead to the surgical instrument via an attachment element coupled to the surgical instrument, the lead having a lead body and an electrode portion, wherein the electrode portion comprises at least one electrode, wherein the surgical instrument urges the electrode portion toward and into stable contact with the target physiological region. The method further comprises transmitting one or more stimulation signals to the target physiological region via the at least one electrode, detecting at least one physiological response to the at least one stimulation signal, and generating mapping data associated with the physiological region based on the at least one physiological response.

In Example 20, the method of Example 19, further comprising adjusting a pressure exerted upon the target physiological region by the electrode portion via a biasing element on the surgical instrument.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
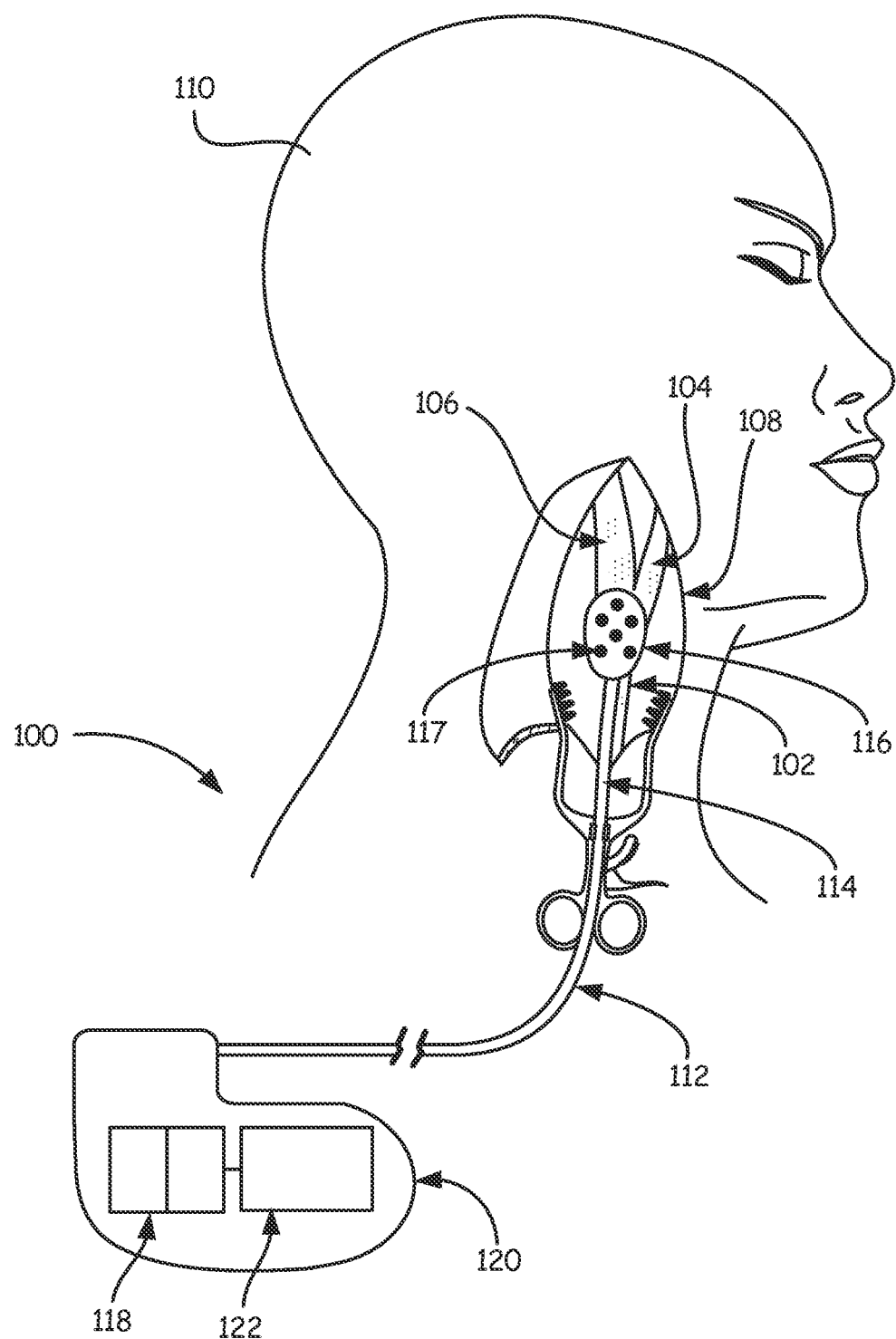
FIG. 1 is a schematic illustration of an implantable stimulation system according to various embodiments.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic illustration showing an example implantable stimulation system 100 configured to sense and stimulate a target physiological region. In some embodiments, the target physiological region may be the vascular tissue and/or the carotid sinus of a patient, which consists of multiple layers of fascia wrapping the common carotid artery 102, the internal carotid artery 104, and the external carotid artery 106. The carotid sinus may be accessed by an incision 108 in the fascia or other tissue of a patient 110. Generally speaking, the internal carotid artery 104 may include a number of baroreceptors, which an operator may seek to target during a therapy procedure. To determine an optimal location at which to place one or more electrodes used in such a therapy procedure, the operator may first map the target physiological region.

As shown, the stimulation system 100 includes a lead 112 with a lead body 114 and an electrode portion 116 including a plurality of electrodes 117. The lead 112 may be a conventional lead, such as a paddle lead or leads designed to work with the stimulation system 100. In various embodiments, the lead body 114 is generally flexible to allow for patient movement. In some embodiments, the lead body 114 can include one or more guide lumens (not shown) to receive a guide member such as a guide wire or stylet in order to support the lead body 114 during surgical implantation. In some embodiments, the medical device lead 112 can be a chronically implanted lead. In some embodiments, the medical device lead 112 can be a temporary lead. In some embodiments, the medical device lead 112 can be an acute lead.

In some examples, the lead 112 is operatively coupled to electronic components 118 located in a pulse generator 120, which may be configured to receive and process one or more detected signals from electrode portion 116. In an aspect, pulse generator 120 may also include a power source 122, which may be a battery or any other source of electrical power for applying an electric potential to one or more electrodes of the electrode portion 116 via one or more conductors integral to lead 112. Thus, when electrical voltage is applied to the conductors of the lead 112, the electrode portion 116 stimulates the target physiological region as a result of the applied voltage during a mapping operation.

In the embodiment illustrated in FIG. 1, the target physiological region is the carotid sinus and the baroreceptors distributed therein. The electrodes 117 are each configured to stimulate the baroreceptors of the carotid sinus for therapeutic purposes such as to control hypertension. For example, the power source 122 may send stimulation signals to the electrode portion 116, thereby applying an electric potential to the electrodes 117, which stimulates the baroreceptors.

Figure 2:
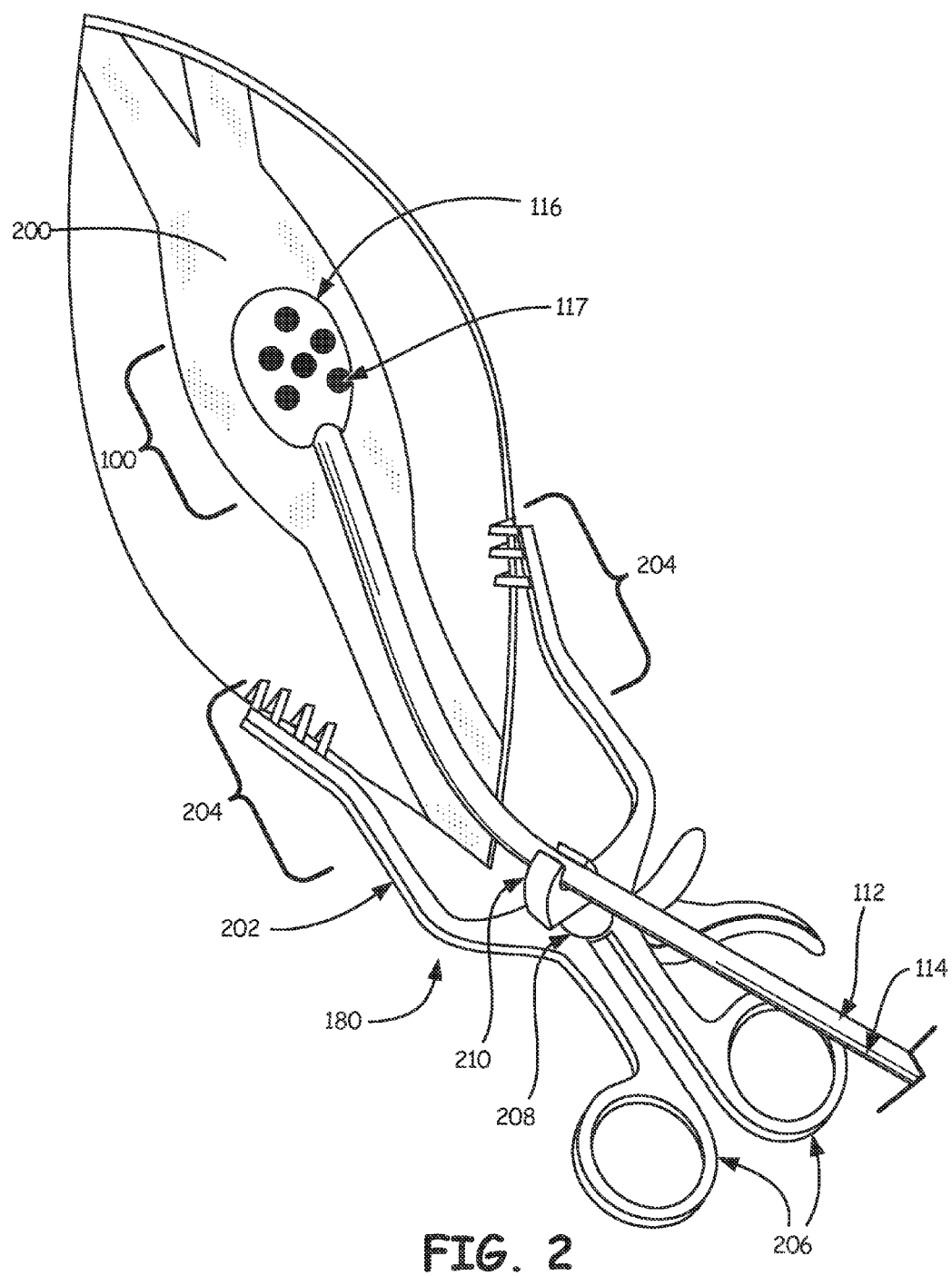
FIG. 2 is an illustration of a medical apparatus in use during the implantation of a medical device lead of the stimulation system of FIG. 1 according to one embodiment.
Figure 3:
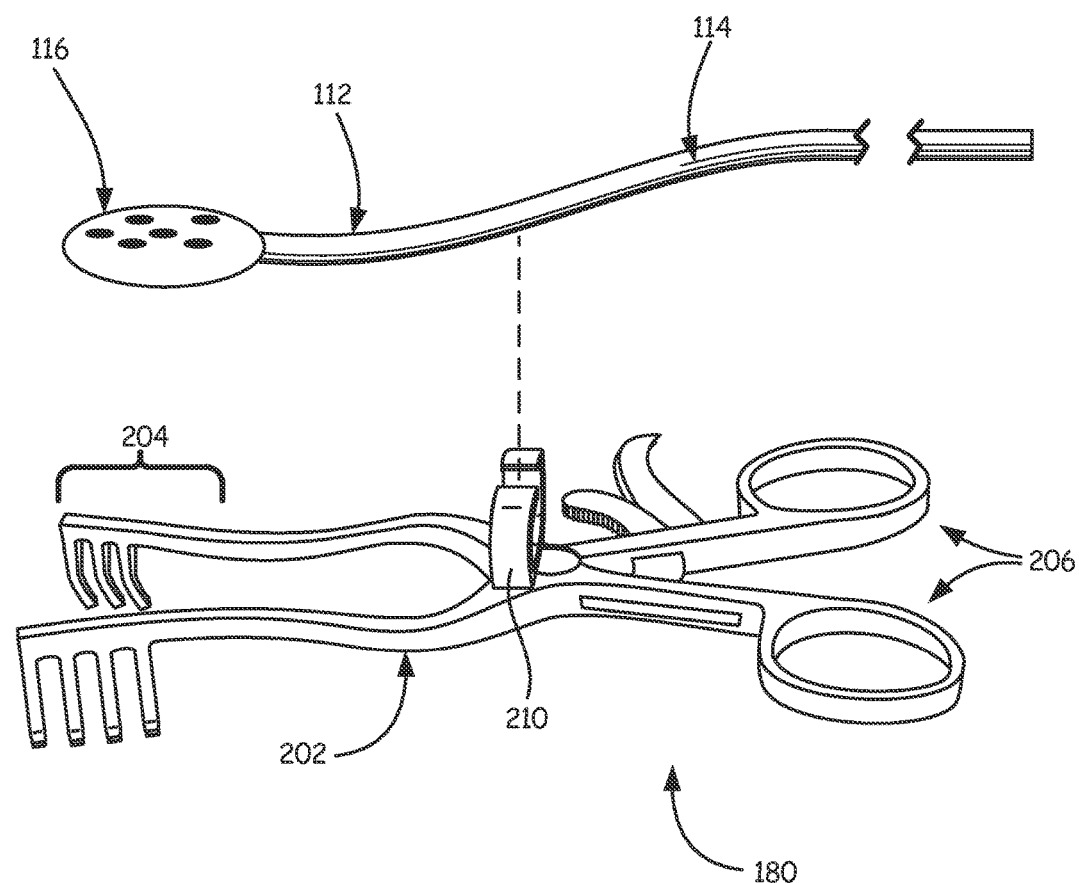
FIG. 3 is a perspective illustration of the medical apparatus and medical device lead shown in FIG. 2 according to one embodiment.

FIG. 2 is an illustration of a medical apparatus 180 in use during the implantation of the medical device lead 112 of the stimulation system 100 at a target physiological region 200 according to one embodiment. FIG. 3 is a perspective illustration of the medical apparatus 180 and the medical device lead 112 according to one embodiment. As shown in FIG. 2, in the illustrated embodiment, the medical apparatus 180 can include a surgical instrument 202 having a pair of instrument portions, each of which may include clamps 204 connected to one or more handles 206. As shown, each of the instrument portions may be coupled together at a pivot point 208. Thus, in use, an operator may spread the clamps 204 apart by applying an inward (or outward, in some examples) pressure on one or both of the handles 206 and may lock the surgical instrument 202 in a desired position, for example, to securely couple the surgical instrument 202 to the patient and to hold tissue open to expose the target physiological region 200. In some embodiments, the surgical instrument 202 can provide the operator with visual access to the target physiological region 200. In various embodiments, the surgical instrument 202 can be a retractor or other instrument used in the surgical field (e.g., a Weitlaner retractor) that can be securely coupled to a patient to open a site on a patient to allow access to a target physiological region.

As further shown in FIG. 2, the medical apparatus 180 includes an attachment element 210 that can be coupled to one or both of the handles 206 of the surgical instrument 202 and/or the pivot point 208. The attachment element 210 may be configured to accept the lead body 114 to stabilize the lead 112 during a mapping procedure and/or other aspects of the implantation procedure.

As can be seen in FIG. 3, the lead body 114 may be releasably coupled to surgical instrument 202 via the attachment element 210. For example, in one embodiment, the attachment element 210 may be configured to receive the lead body 114 when a force is applied to the lead body 114 in the direction of the attachment element 210. In the particular embodiment shown in FIGS. 2 and 3, attachment element 210 is configured to receive and releasably engage the lead body 114 in a snap-fit arrangement. In other embodiments, as described additionally herein, the attachment element 210 can be configured to employ other techniques for releasably engaging the lead body 114 and coupling the lead body 114 to the surgical instrument 202. In the various embodiments, by releasably securing the lead body 114 to the surgical instrument 202, the electrode portion 116 can be maintained in a stable position in contact with the target physiological region 200 without requiring the implanting physician to manually hold the lead body 114. In other words, when the lead body 114 has been received by the attachment element 210, the lead 112 and its electrode portion 116 can be securely held in place as the electrode portion 116 contacts the target physiological region 200 during mapping thereof.

Figure 4A:
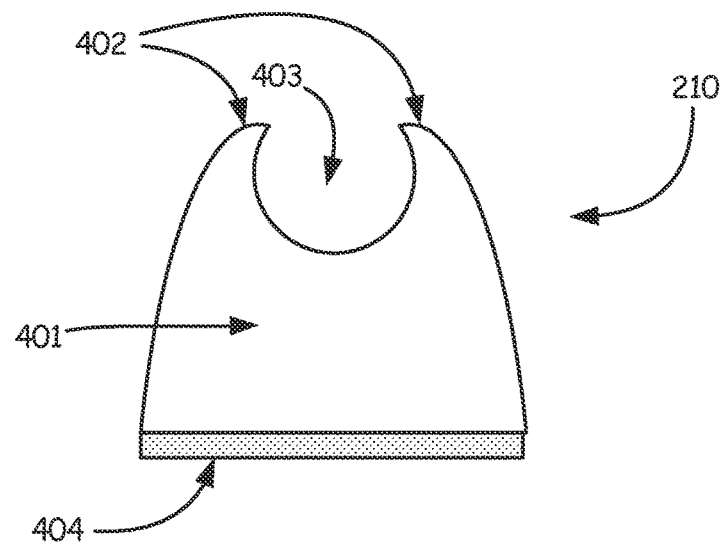
FIGS. 4A and 4B are elevation views of an exemplary attachment element of the medical apparatus of FIGS. 1 and 2 according to one embodiment.
Figure 4B:
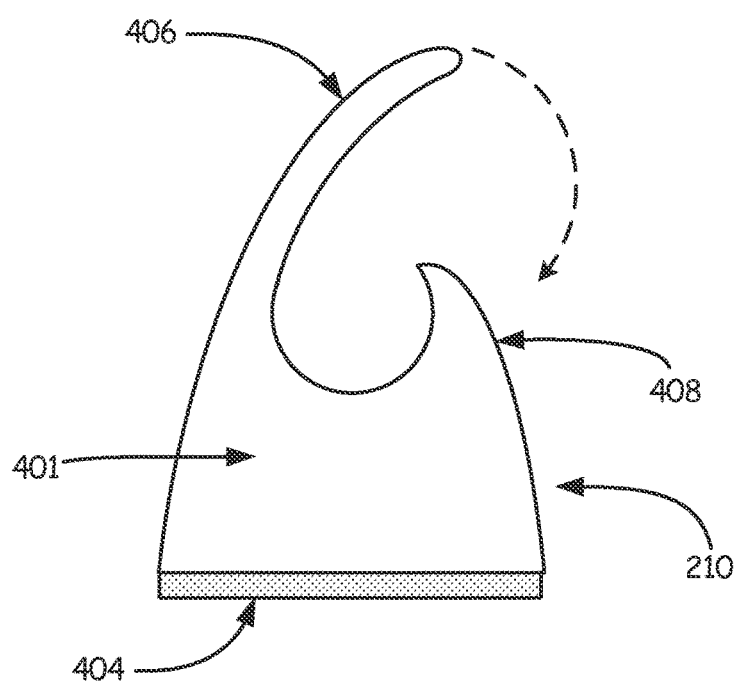

FIGS. 4A and 4B illustrate non-limiting examples of the attachment element 210 according to various embodiments.

As shown in FIG. 4A, in one embodiment, the attachment element 210 may include a body 401 having a curved clip 402 sized to form a lead body-receiving opening 403. In various embodiments, the clip 402 is configured to receive and releasably engage the lead body 114, thereby inhibiting relative movement of the lead body 114 and the attachment element 210. The lead body 114 may snap-fit or press-fit into the clip 402 and may require sufficient force to inhibit unintended detachment of the lead body 114 from the attachment element 210. In various embodiments, the clip 402 may have grooves or projections that are designed to fit the lead body 114.

Alternatively, as shown in FIG. 4B, the attachment element 210 may, in another embodiment, include a flexible arm 406 and associated arm-securing portion 408 for receiving and coupling the flexible arm 406 to the arm-securing portion. In some examples, the flexible arm 406 can be snap fit or secured to the arm-securing portion 408 to form a loop. The lead body 114 can be secured within the loop. Additionally, in an aspect, the flexible arm 406 is flexible enough to bend. Also, in some embodiments, the flexible arm 406 includes a swivel or hinge mechanism to form the lead securing portion.

In various embodiments, the attachment element 210 may be an integral component of the surgical instrument 202. In various embodiments, the attachment element 210 may be a separate component from the surgical instrument 202, and may be coupled to the surgical instrument 202 prior to or during the particular lead implantation procedure. In one embodiment, for example, the attachment element can be attached to the surgical instrument 202 using adhesive 404 on a lower side of the attachment element 210. In other embodiments, any adhesive or a suitable coupling mechanism known in the art may be used. For example, in some embodiments, a friction fit or a mechanical fastener (e.g., a screw) or a clamping mechanism may be used to secure the attachment element 210 to the surgical instrument 202. In such embodiments, the attachment element 210 can be either releasably or permanently coupled to the surgical instrument 202.

In various embodiments, the medical apparatuses of the present disclosure may include a biasing element configured to vary the intensity of pressure applied to the target physiological region by the electrode portion 116 (FIG. 1). Variation in the application pressure may help the operator to reliably apply stimulation signals to the target physiological region and to accurately detect a response of the baroreceptors to the one or more stimulation signals.

Figure 5:
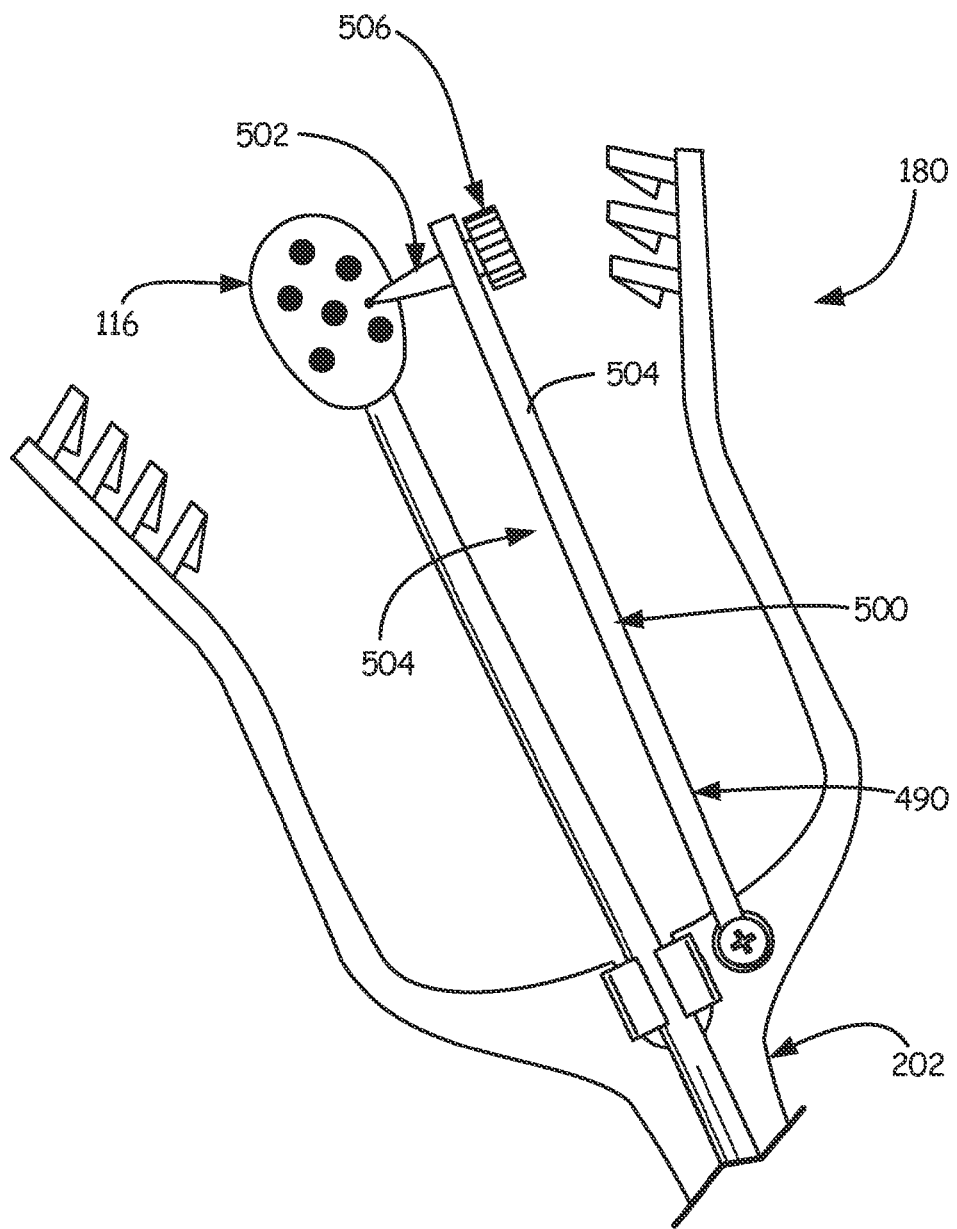
FIG. 5 is an elevation view of a portion of an alternative medical apparatus and medical device lead according to one embodiment.
Figure 6:
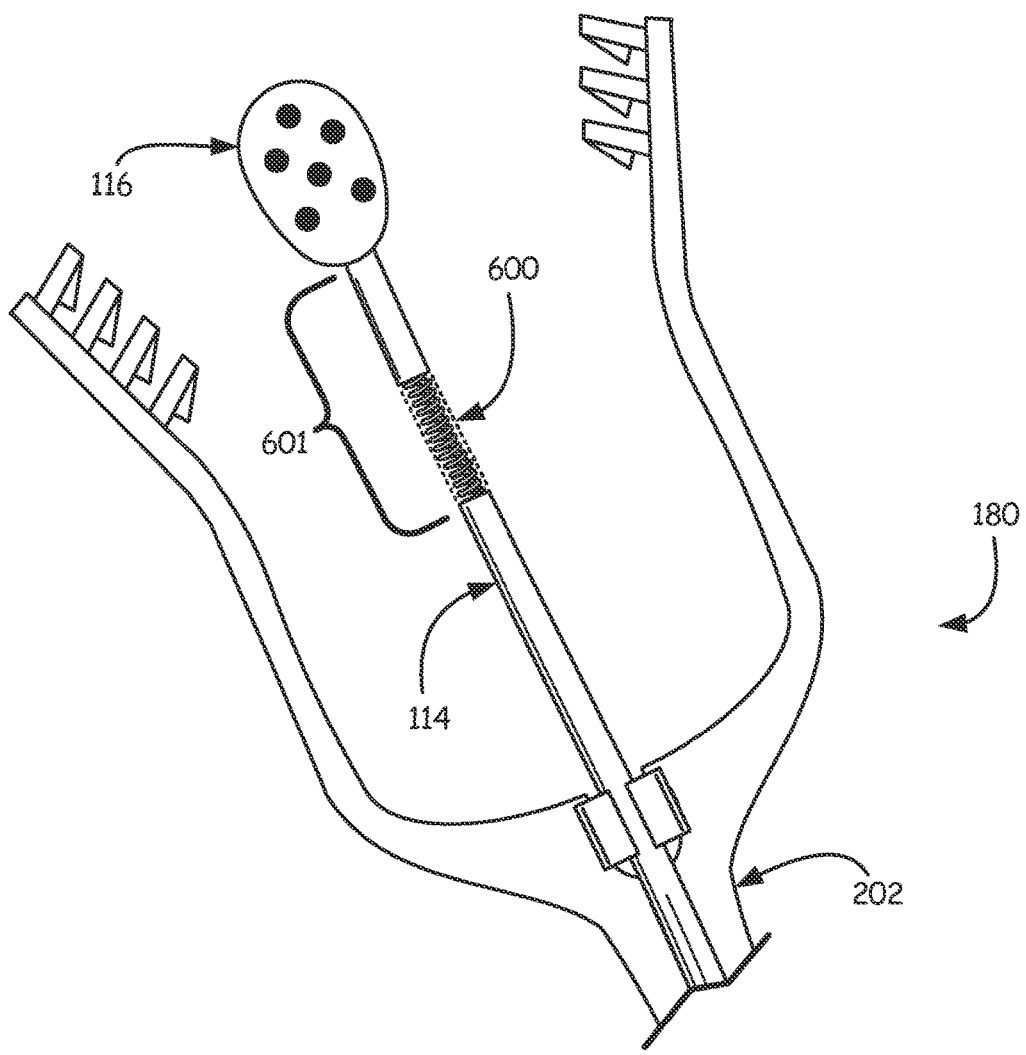
FIG. 6 is an elevation view of a portion of a medical apparatus and medical device lead according to one embodiment.
Figure 7:
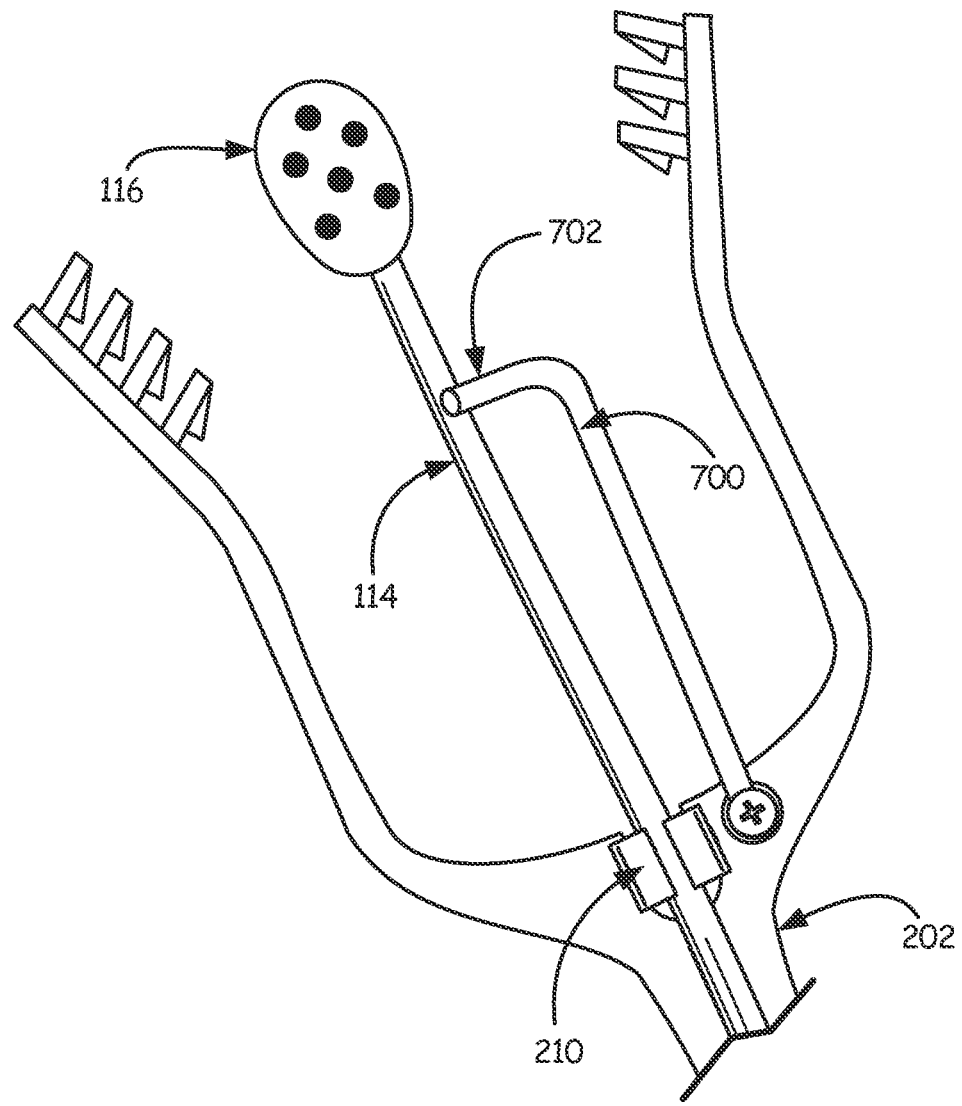
FIG. 7 is an elevation view of a portion of a medical apparatus and medical device lead according to one embodiment.

FIGS. 5-7 are elevation views of portions of alternative medical apparatuses 180 and medical device leads 112 according to various embodiments wherein the surgical instrument 202 and/or the lead 112 includes at least one biasing element. In the embodiment shown in FIG. 5, the medical apparatus 180 includes a surgical instrument 202 similar to those described in connection with FIGS. 2-4A/B, modified to include a biasing element 490. In the illustrated embodiment, the biasing element 490 may be an axial adjustment element 500. The axial adjustment element 500 may include an axial adjustment head 502 that is configured to move along an axis substantially orthogonal to the plane of the electrode portion 116. Additionally, the axial adjustment head 502 may be coupled to an axial adjustment element support 504, which may be connected to the attachment element 210 (FIGS. 2-4). In additional or alternative examples, the axial adjustment element support 504 may be directly coupled to the surgical instrument 202 (FIG. 2). The axial adjustment element support 504 may be operable to exert a downward pressure bias on the electrode portion 116 via the axial adjustment head 502. Moreover, axial adjustment element support 504 may be composed of a material sufficient to withstand the pressure applied to the target physiological region without significantly deforming, which may include, but is not limited to, a metal or rigid plastic material. In other examples, the axial adjustment element support 504 may be composed of a pliant material that may be manipulated by the operator to adjust the pressure or angle of the axial adjustment tool vis-à-vis the surgical instrument 202. For example, in some examples, the operator may adjust the applied pressure by bending a pliant axial adjustment element support 504 toward or away from the target physiological region along the axis orthogonal to the plane of the electrode portion 116.

Furthermore, the axial adjustment head 502 may include an axial adjustment screw 506 configured to adjust an application pressure when turned radially. For example, in one embodiment, rotation of the axial adjustment screw 506 by the physician causes the axial adjustment head 502 to be advanced along an adjustment axis toward the electrode portion 116 so as to cause the electrode portion 116 to apply increased pressure against the target physiological region. Likewise, when turned in an opposite direction, the axial adjustment screw 506, and consequently, the axial adjustment head 502, may be retracted away from the target physiological region to decrease the amount of pressure applied thereto by the electrode portion 116. As such, the axial adjustment screw 506 may be configured to allow for fine adjustment so that an optimum application pressure can be reached and maintained on the electrode portion 116 and the target physiological region.

Turning to FIG. 6, in some embodiments, the biasing element can take the form of a spring 600 may be disposed in a neck area 601 of the lead body 114. In the illustrated embodiment, the neck area 601 is located near and proximal to the electrode portion 116. In some embodiments, the spring 600 may be configured so as to bias the electrode portion 116 toward the target physiological region and thereby exert a relatively constant spring force against the target physiological region. In additional or alternative embodiments, the spring 600 can be adjustable to allow spring manipulation by the operator. For example, the spring 600 may be constructed of a material that allows manual manipulation and positional memory such that the pressure of the electrode portion 116 against the target physiological region may be adjusted and maintained after adjustment. Furthermore, spring 600 may be integral to a sheathing of lead body 114 or may be external to the lead body 114, so long as pressure adjustment via the spring 600 is feasible.

In some embodiments of the medical apparatus 180, the biasing element may be a guide mechanism 700 connected to and extending distally from one or both of the surgical instrument 202 or the attachment element 210, as shown in FIG. 7. In one embodiment, the guide mechanism 700 may be configured to exert an application pressure against the lead body 114 and/or the electrode portion 116, so as to urge the electrode portion 116 toward the target physiological region 200. In an aspect, a distal end 702 of the guide mechanism 700 is bent towards the lead body 114 and a proximal end of the guide mechanism 700 is coupled to the attachment element 210 and/or the surgical instrument 202. To allow bending by the operator, the guide mechanism 700 may be composed of a pliant or flexible material and configured to maintain or apply the application pressure on the lead body 114 after being bent. In some embodiments, the biasing element, such as biasing element 490 or guide mechanism 700, can be made integral with the attachment element 210.

Figure 8:
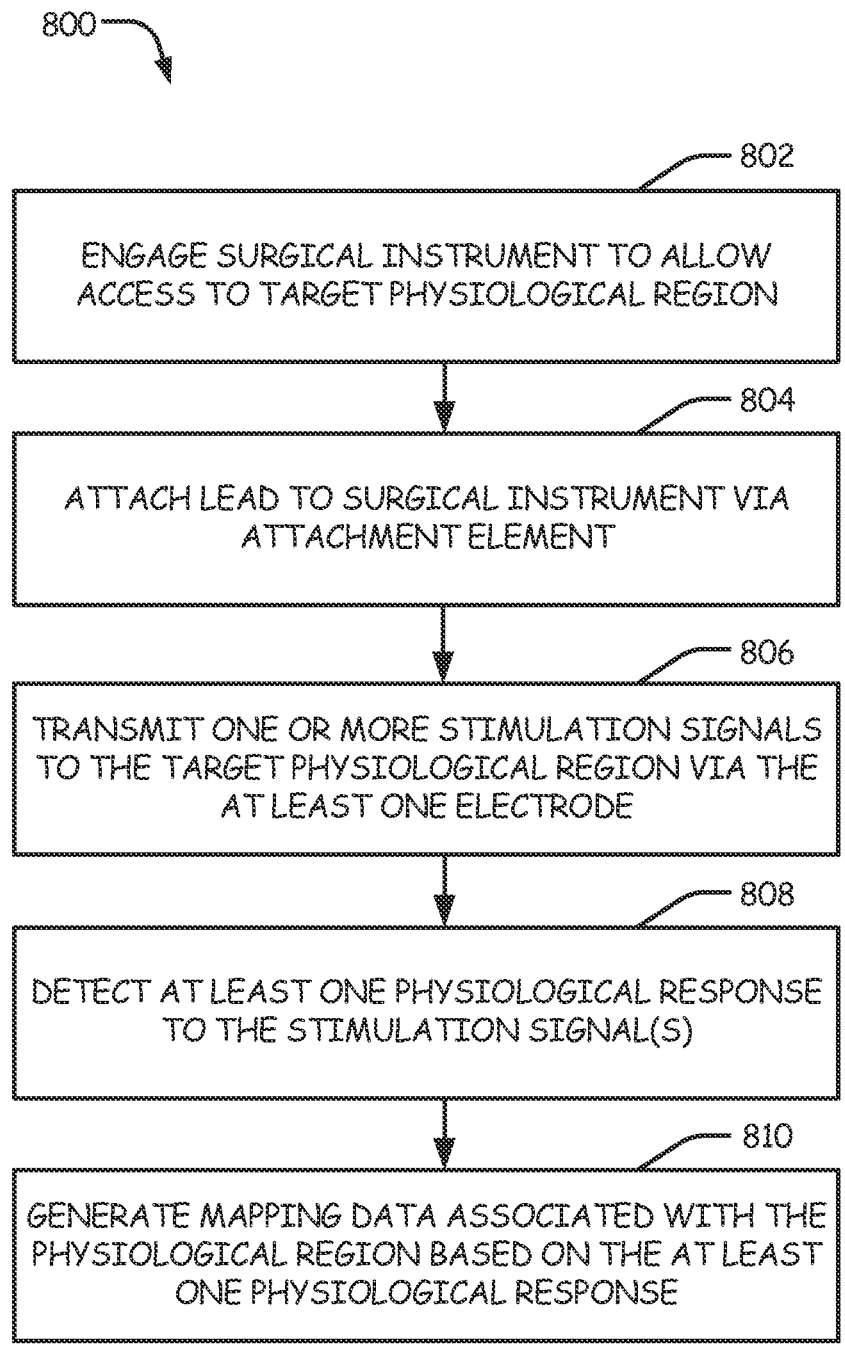
FIG. 8 is a flow chart illustrating an exemplary method of mapping a target physiological region using the medical apparatus of FIG. 2.

FIG. 8 illustrates an example methodology 800 for mapping a target physiological region of a patient. Methodology 800 may include several steps represented in FIG. 8 as functional blocks. These steps of methodology 800 may be performed in the order presented in FIG. 8, but may also be performed in any other order. Furthermore, the steps illustrated in FIG. 8 are not exclusive or limiting.

In an example, methodology 800 may include, at block 802, coupling a surgical instrument to the patient to allow access to the target physiological region. In an aspect, this may include placing a retractor at an incision site such that the incision is held open by the retractor. Additionally, methodology 800 may include, at block 804, attaching a lead to the surgical instrument via an attachment element. In an aspect, the lead may have a lead body and an electrode portion, where the electrode portion comprises at least one electrode. Furthermore, at block 806, methodology 800 may include transmitting one or more stimulation signals to the target physiological region via the at least one electrode. Moreover, at block 808, methodology may include detecting at least one physiological response to the at least one stimulation signal via the at least one electrode. In addition, methodology 800 may include, at block 810, generating mapping data associated with the physiological region based on the at least one physiological response. In various embodiments, if the desired physiological response is not attained, the physician may detach the lead body from the surgical instrument, reposition the electrode portion at a different physiological region, and thereafter, repeat the methodology 800 beginning at block 804.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical apparatus comprising:
   a surgical instrument configured to be securely coupled to a patient and to allow access to a target physiological region; and
   an attachment element coupled to the surgical instrument and configured to releasably engage an implantable medical device lead,
   wherein the surgical instrument includes first and second instrument portions each including a clamp portion and a handle portion opposite the clamp portion, wherein the first and second instrument portions are pivotally coupled to one another between the respective handle and clamp portions such that an application of an inward force urging the handle portions toward one another causes the clamp portions to one of separate from one another and close toward one another.

2. The medical apparatus of claim 1, wherein the implantable medical device lead comprises a lead body and an electrode portion, wherein the electrode portion comprises at least one electrode configured to apply at least one stimulation signal to the target physiological region, and wherein the surgical instrument is configured to urge the electrode portion into stable contact with the target physiological region when the surgical instrument is coupled to the patient.

3. The medical apparatus of claim 1, further comprising a biasing element attached to at least one of the surgical instrument and the attachment element, wherein the biasing element is configured, in use, to urge the electrode portion of the implantable medical device lead toward the target physiological region and cause the electrode portion of the implantable medical device lead to apply pressure to the target physiological region when the implantable medical device lead is coupled to the attachment element and the surgical instrument is coupled to the patient.

4. The medical apparatus of claim 3, wherein the biasing element is composed at least in part of a pliant material and is configured to urge the electrode portion of the implantable medical device lead toward the target physiological region upon an application of bending stress to the biasing element when the implantable medical device lead is coupled to the attachment element and the surgical instrument is coupled to the patient.

5. The medical apparatus of claim 3, wherein the biasing element comprises an axial adjustment element comprising an axial adjustment element support and an axial adjustment head, wherein a position of the axial adjustment head is selectively adjustable along an adjustment axis.

6. The medical apparatus of claim 5, wherein the axial adjustment head comprises an adjustment screw configured to cause the adjustment head to move along the adjustment axis upon rotation of the adjustment screw.

7. The medical apparatus of claim 1, wherein the attachment element comprises a lead clip configured to receive and engage the lead body.

8. The medical apparatus of claim 1, wherein the attachment element comprises a flexible arm configured to substantially enclose a portion of the lead body inside an attachment element enclosure formed when the flexible arm is placed over the lead body and secured to an arm securing portion of the attachment element.

9. The medical apparatus of claim 1, wherein the attachment element is releasably coupled to the surgical instrument.

10. The medical apparatus of claim 1, wherein the surgical instrument is further configured to maintain visual access to the target physiological region when coupled to the patient.

11. The medical apparatus of claim 1, wherein the attachment element is coupled to one or both of the first and second instrument portions.

12. The medical apparatus of claim 1, wherein the surgical instrument comprises at least one of a Weitlaner retractor, a Mayo-Adams retractor, a Rigby retractor, and a Gelpi retractor.

13. A medical kit comprising:
a surgical instrument configured to be securely coupled to a patient and to allow access to a target physiological region;
an attachment element coupled to the surgical instrument;
an implantable medical device lead comprising a lead body and an electrode portion, wherein the electrode portion comprises at least one electrode configured to apply at least one stimulation signal to the target physiological region,
wherein the attachment element is configured to releasably engage the lead body and the surgical instrument is configured to urge the electrode portion into contact with the target physiological region when the lead body is engaged by the attachment element and the surgical instrument is coupled to the patient; and
a biasing element attached to at least one of the surgical instrument and the attachment element, wherein the biasing element is configured, in use, to urge the electrode portion of the implantable medical device lead toward the target physiological region and cause the electrode portion of the implantable medical device lead to apply pressure to the target physiological region when the implantable medical device lead is coupled to the attachment element and the surgical instrument is coupled to the patient, wherein the biasing element comprises an axial adjustment element comprising an axial adjustment element support and an axial adjustment head, wherein a position of the axial adjustment head is selectively adjustable along an adjustment axis.

14. The medical kit of claim 13, wherein the lead body includes neck region proximal to the electrode portion, the neck region including a spring disposed within the lead body.

15. The medical kit of claim 13, wherein the biasing element is composed at least in part of a pliant material and configured to urge the electrode portion of the implantable medical device lead toward the target physiological region upon an application of bending stress to the biasing element when the implantable medical device lead is coupled to the attachment element and the surgical instrument is coupled to the patient.

16. A method of mapping a target physiological region of a patient, comprising:
coupling a surgical instrument to the patient to allow access to the target physiological region;
coupling a lead to the surgical instrument via an attachment element coupled to the surgical instrument, the lead having a lead body and an electrode portion that comprises at least one electrode and the surgical instrument urges the electrode portion toward and into contact with the target physiological region, wherein coupling the lead to the surgical instrument via the attachment element includes releasably securing the lead body in the attachment element and maintaining the electrode portion spaced away from the attachment element;
transmitting one or more stimulation signals to the target physiological region via the at least one electrode;
detecting at least one physiological response to the at least one stimulation signal; and
generating mapping data associated with the physiological region based on the at least one physiological response.

17. The method of claim 16, further comprising adjusting a pressure exerted upon the target physiological region by the electrode portion via a biasing element on the surgical instrument.

* * * * *